United States Patent
Huang (10) Patent No.: US 11,963,976 B2
(45) Date of Patent: Apr. 23, 2024

(54) HEPARIN COMPOSITION FOR TREATING ISCHEMIA

(71) Applicant: National Cheng Kung University, Tainan (TW)

(72) Inventor: Lynn L. H. Huang, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 16/642,291

(22) PCT Filed: Sep. 5, 2018

(86) PCT No.: PCT/US2018/049466
§ 371 (c)(1),
(2) Date: Feb. 26, 2020

(87) PCT Pub. No.: WO2019/050893
PCT Pub. Date: Mar. 14, 2019

(65) Prior Publication Data
US 2021/0077522 A1    Mar. 18, 2021

Related U.S. Application Data

(60) Provisional application No. 62/554,101, filed on Sep. 5, 2017.

(51) Int. Cl.
| | | |
|---|---|---|
| *A61K 31/727* | (2006.01) | |
| *A61K 9/00* | (2006.01) | |
| *A61K 31/728* | (2006.01) | |
| *A61K 47/36* | (2006.01) | |
| *A61P 9/10* | (2006.01) | |
| *C07K 14/49* | (2006.01) | |
| *A61K 45/06* | (2006.01) | |

(52) U.S. Cl.
CPC .......... *A61K 31/727* (2013.01); *A61K 9/0024* (2013.01); *A61K 31/728* (2013.01); *A61K 47/36* (2013.01); *A61P 9/10* (2018.01); *C07K 14/49* (2013.01); *A61K 45/06* (2013.01)

(58) Field of Classification Search
CPC ...... A61K 31/727; A61K 31/72; A61K 47/36; A61K 31/728; A61P 9/10; A61P 19/02; A61P 27/04; A61P 41/00
See application file for complete search history.

(56) References Cited

U.S. PATENT DOCUMENTS

| | | |
|---|---|---|
| 4,636,524 A | 1/1987 | Balazs et al. |
| 8,192,718 B1 | 6/2012 | Sung et al. |
| 2005/0043271 A1* | 2/2005 | Gross .................. A61K 31/727 514/54 |
| 2005/0271730 A1 | 12/2005 | Dellacherie et al. |
| 2011/0008444 A1* | 1/2011 | Bergman ............ C08B 37/0072 424/488 |
| 2011/0201572 A1* | 8/2011 | Lopez-Belmonte Encina ............. A61K 31/727 514/56 |
| 2011/0311653 A1 | 12/2011 | Kevil et al. |
| 2012/0208757 A1 | 8/2012 | Huang |
| 2014/0315805 A1 | 10/2014 | Carmichael et al. |

FOREIGN PATENT DOCUMENTS

| | | |
|---|---|---|
| WO | WO-2005/063807 A2 | 7/2005 |
| WO | WO 2012/048214 A2 | 4/2012 |
| WO | WO-2012/162555 A2 | 11/2012 |

OTHER PUBLICATIONS

Bhakta, G. et al "Hyaluronic acid-based hydrogels functionalized with heparin . . . " Biomaterials, vol. 33, issue 26, pp. 6113-6122. (Year: 2012).*
Kiesel, M. et al "Complexation and sequestation of BMP-2 . . . " Plos One, vol. 8, iss 10, pp. 1-12. (Year: 2013).*
Krishnan, L. et al "Vascularization strategies for bone regeneration" Ann. Biomed. Eng., vol. 42, No. 2, pp. 432-444. (Year: 2014).*
White, C. et al "Bringing comfort to the masses . . . " Contact Lens & Anter. Eye, vol. 37, pp. 81-91. (Year: 2014).*
Product information for Heparin sodium salt https://www.sigmaaldrich.com/deepweb/assets/sigmaaldrich/product/documents/112/608/h3393pis.pdf Retrieved Jul. 16, 2021. (Year: 2015).*
Zhang, Z. et al "The nonlinear viscoelasticity of hyaluronic . . . " Soft Matter, vol. 11, pp. 2596-2603. (Year: 2015).*
Theocharis, A. et al "Extracellular matrix structure" Adv. Drug Deliv. Rev., vol. 97, pp. 4-27. (Year: 2016).*
Young, Y. et al "Controlled release of heparin-binding growth factors . . . " Exp. Opin. Drug Deliv., vol. 5, No. 11, pp. 1173-1184. (Year: 2008).*
Durmaz CE, et al "Comparison of effects of unfractionated heparin and low molecular weight heparin on skin wound healing of rats." Acta Cirúrgica Brasileira vol. 27, pp. 639-644. (Year: 2012).*
Hu, M. et al "Tissue engineering and regenerative repair in wound healing" Ann. Biomed. Eng., vol. 42, No. 7, pp. 1494-1507. (Year: 2014).*
Nih et al "Dual-Function Injectable Angiogenic Biomaterial for the Repair of Brain Tissue Following Stroke" Nature Materials vol. 17, pp. 642-653, 2018.
Nih et al "Engineered HA Hydrogel for Stem Cell Transplantation in the Brain: Biocompatibility Data Using a Design of Experiment Approach" Data in Brief vol. 10, pp. 202-209, 2017.
Nih et al "Hydrogels for Brain Repair After Stroke: An Emerging Treatment Option" Current Opinion in Biotechnology vol. 40, pp. 155-163, 2016.

(Continued)

*Primary Examiner* — Leigh C Maier
(74) *Attorney, Agent, or Firm* — Morse, Barnes-Brown & Pendleton, P.C.; Jeannie Wu, Esq.

(57) ABSTRACT

A pharmaceutical composition for treating an ischemic tissue, comprising: a core component and a matrix component, wherein the core component includes a heparin or derivative thereof and the matrix component includes a hyaluronan or derivative thereof, the pharmaceutical composition having a viscosity greater than 10 mPa-s.

19 Claims, 6 Drawing Sheets

(56) References Cited

OTHER PUBLICATIONS

Zhong et al "Hydrogel Matrix to Support Stem Cell Survival After Brain Transplantation in Stroke" Neurorehabilitation and Neural Repair vol. 24, pp. 636-644, 2010.

Ashikari-Hada, et al. "Heparin Regulates Vascular Endothelial Growth Factor 165-dependent Mitogenic Activity, Tube Formation, and Its Receptor Phosphorylation of Human Endothelial Cells" The Journal of Biological Chemistry; vol. 280, No. 36; pp. 31508-31515; Sep. 9, 2005.

Shen, et al. "Heparin Impairs Angiogenesis through Inhibition of MicroRNA-10B" The Journal of Biological Chemistry; vol. 286; No. 30; pp. 26616-26627; Jul. 29, 2011.

\* cited by examiner

Mean ± SEM, * : $P < 0.05$, ** : $P < 0.01$, n=7

(B)

* : $P < 0.05$, ** : $P < 0.001$, $n_{Normal}=3$ ; $n_{DIB}=4$

FIG. 6

HEPARIN COMPOSITION FOR TREATING ISCHEMIA

CROSS-REFERENCE TO RELATED APPLICATION

This application is the National Stage of International Application No. PCT/US2018/049466, filed on Sep. 5, 2018, which claims priority to U.S. Provisional Application No. 62/554,101, filed on Sep. 5, 2017, the contents of both prior applications being hereby incorporated by reference in their entirety.

BACKGROUND

In ischemia, the blood content of an organ or tissue is reduced. Ischemia can be a local manifestation of systemic anemia or a result of local blood circulation disorders. Types of ischemia include: 1) Compression ischemia can be caused by pressures on the arterial blood vessels from, for example, tumors, tight bandage and effusion, resulting in narrowing or occlusion of the lumen of the blood vessel. Clinically, hemorrhoids or ulcers formed from prolonged lying are instances of tissue necrosis caused by ischemia due to compression of lateral blood vessels, which can lead to muscle damages. 2) Obstructive ischemia from arterial thrombosis or embolism can lead to vascular occlusion, resulting in blocked blood supply to, for example, the limbs or heart. 3) Lateral limb ischemia can be caused by a rapid flow of a large amount of blood into the abdominal organs, resulting in ischemia of other organs and tissues.

Patients with peripheral arterial diseases of the lower limbs are mostly over 60 years old, and about one-half of the patients have diabetes. At present, angiogenesis treatments for ischemic lower limbs are being marketed. For example, the AutoloGel system is a wound dressing prepared by extracting a patient's autologous high-concentration plate-rich plasma (PRP) and adding a growth factor that promotes wound healing and a cytokine to form a gelatinous substance. However, such treatments are only used to treat chronic wounds, but they are not able to treat the underlying ischemia. Other treatments such as bypass grafting, vasodilation, and placement of vascular stents are necessary to resolve vascular occlusion.

Many studies on ischemic lower limbs are actively developing angiogenic therapeutics, such as cytokines or recombinant growth factors associated with angiogenic signaling, such as VEGF and FGF to stimulate angiogenesis. Platelet-derived growth factor (PDGF) has been found to stimulate mesenchymal cell proliferation, migration and differentiation in developmental or adult tissues, and is used to promote the release of endothelial-derived cells from bone marrow of patients to achieve vascular proliferation. Human umbilical vein endothelial cells (HUVEC) can also be stimulated by substances that are indirectly related to angiogenic signaling to stimulate angiogenesis. Treatment using tissue plasminogen activator (tPA) and HUVEC is given to increase the number of endothelial progenitor cells that migrate from the bone marrow to the blood vessels to promote vascular endothelial rejuvenation to achieve therapeutic effects.

In addition to the above-mentioned direct promotion of angiogenesis, studies have found that heparin can be treated with poly(lactic-co-glycolic acid) (PLGA) nanoparticles to achieve therapeutic angiogenesis. Its role is to stimulate the expression of angiogenesis-related growth factors by means of delayed release of drugs. Heparin (also known as unfractionated heparin, fractionated heparin (also known as low molecular weight heparin), and its low-molecular-weight derivatives (e.g., enoxaparin, dalteparin, and tinzaparin) are effective for preventing deep vein thromboses and pulmonary emboli. They are typically administered intravenously or subcutaneously.

The physiological condition of hyperglycemia caused by diabetes reduces the secretion of endothelial growth factor which, in the cases of severe vascular diseases, can lead to amputations. Most of the current treatment methods involve angiogenic factors, which face many difficulties in clinical use or medical efficacy. Nowadays, there is still no effective therapy to regenerate ischemia tissues, nonetheless to rescue limbs from amputation. Therefore, the development of a therapeutic composition for ischemia tissues suitable for most patients is an important problem to be solved.

SUMMARY

In one aspect, described herein is a pharmaceutical composition for treating an ischemic tissue. The pharmaceutical composition contains a core component and a matrix component, wherein the core component includes a heparin or derivative thereof and the matrix component includes a hyaluronan or derivative thereof, the pharmaceutical composition having a viscosity greater than 10 mPa·s. In some embodiments, the viscosity is 10 to 10000 mPa·s. In some embodiments, the viscosity is within the range of viscosities of 3 to 10 mg/ml of hyaluronan having a mean molecular weight of 700 to 2000 kDa. In some embodiments, the viscosity is the same as the viscosity of 5 mg/ml of hyaluronan having a mean molecular weight of 1560 kDa.

In some embodiments, hyaluronan has a mean molecular weight of 100 kDa to 5000 kDa (e.g., 700 kDa to 2000 kDa). In some embodiments, the pharmaceutical composition contains 1 mg/ml to 100 mg/ml of the hyaluronan. The mean molecular weight of the hyaluronan can be 700 to 2000 kDa and the concentration of the hyaluronan can be 3 to 10 mg/ml. In some embodiments, the mean molecular weight of the hyaluronan is 1560 kDa and the concentration of the hyaluronan is 5 mg/ml.

The heparin or derivative thereof in the pharmaceutical composition can be selected from the group consisting of unfractionated heparin (UFH), fractionated heparin (low molecular weight heparin), heparinoid, enoxaparin, dalteparin, or tinzaparin. In some embodiments, the pharmaceutical composition contains the heparin or derivative thereof at 0.00001 U to 20 U per 100 μl of the pharmaceutical composition.

In some embodiments, the matrix component further includes a collagen, an extracellular matrix factor, a protein, or a polysaccharide.

In some embodiments, the core component further includes a thrombolytic drug or angiogenic compound. The thrombolytic drug or angiogenic compound can be selected from the group consisting of ticlopidine, warfarin, tissue plasminogen activator, eminase, retavase, streptase, tissue plasminogen activator, tenecteplase, abbokinase, kinlytic, urokinase, prourokinase, anisoylated purified streptokinase activator complex (APSAC), fibrin, plasmin, and vascular endothelial growth factor (VEGF).

In another aspect, provided herein is a method of treating an ischemic tissue in a subject. The method includes administering the pharmaceutical composition described herein directly to the ischemic tissue in a subject, provided that the pharmaceutical composition is not administered intravenously. In some embodiments, the pharmaceutical composition is administered intramuscularly. The ischemic tissue can be an ulcer, or in a heart or limb in a subject.

In some embodiments, the ischemic tissue is an ulcer, or in a heart or limb in a subject. The ischemic tissue can be a muscle. In some embodiments, the subject has diabetes.

The details of one or more embodiments are set forth in the accompanying drawing and the description below. Other features, objects, and advantages of the embodiments will be apparent from the description and drawing, and from the claims.

DETAILED DESCRIPTION

It was unexpectedly discovered that a pharmaceutical composition containing hyaluronan having certain viscosity and a heparin was effective for treating ischemic tissues.

Pharmaceutical Composition

Accordingly, described herein is a pharmaceutical composition for treating an ischemic tissue. The pharmaceutical composition includes a core component and a matrix component, the core component including a heparin and the matrix component including a hyaluronan or derivative thereof. The pharmaceutical composition has a viscosity greater than 10 mPa·s. Depending on the parameters selected for measuring viscosity (e.g., the spindle and rotation speed), the viscosity of the composition may range from 10 to 10000 mPa·s (e.g., 10-100, 50-150, 100-200, 150-250, 250-500, 500-1000, 1000-1500, 1500-2000, 2000-2500, 2500-3000, 3000-3500, 3500-5000, 5000-6000, 6000-7000, 7000-8000, 8000-9000, or 9000-10000).

The viscosity of the pharmaceutical composition can fall within the range of the viscosities of 3 to 10 mg/ml (e.g., 3, 3.5, 4, 4.5, 5, 5.5, 6, 6.5, 7, 7.5, 8, 8.5, 9, 9.5, or 10 mg/mi) of hyaluronan having a mean molecular weight of 700 to 2000 kDa (e.g., 700, 800, 900, 1000, 1500, 1600, 1700, 1800, 1900, or 2000). See Tables 2-5 below. In some embodiments, the viscosity of the composition is the same as the viscosity of 5 mg/ml of hyaluronan having a mean molecular weight of 1560 kDa. For example, data described below show that 4 mg/ml of 2000 kDa hyaluronan, 5 mg/ml of 1,560 kDa hyaluronan, and 6.5 mg/ml 700 kDa hyaluronan have about the same viscosity.

The molecular weight of the hyaluronan in the pharmaceutical composition can range from 4 kDa to 5000 kDa (e.g., 4 to 20, 20 to 100, 100 to 500, 500 to 1000, 1000 to 2000, 2000 to 2500, 2500 to 5000, 5, 10, 50, 100, 200, 300, 400, 500, 750, 1000, 1500, 1800, 2000, 2500, 3000, 3500, 4000, 4500, or 5000 kDa). The concentration of the hyaluronan in the pharmaceutical composition can be 1 to 100 mg/ml (e.g., 1, 1.5, 2, 2.5, 3, 3.5, 4, 4.5, 5, 5.5, 6, 6.5, 7, 7.5, 8, 8.5, 9, 9.5, 10, 20, 30, 40, 50, 60, 70, 80, 90, or 100 mg/mi). In particular, the concentration of the hyaluronan in the pharmaceutical composition can be 3 to 10 mg/ml (e.g., 3, 3.5, 4, 4.5, 5, 5.5, 6, 6.5, 7, 7.5, 8, 8.5, 9, 9.5, or 10 mg/ml) if using hyaluronan having a mean molecular weight of 700 to 2000 kDa. A skilled practitioner would be able to select the appropriate combination of molecular weight and concentration to achieve a composition having the desired viscosity. A skilled practitioner would also be able to determine the viscosity of a composition using methods known in the art and commercially available instruments.

The heparin in the pharmaceutical composition can be a heparin or a derivative thereof. The heparin can be selected from the group consisting of unfractionated heparin (UFH), fractionated heparin (low molecular weight heparin), heparinoid, enoxaparin, dalteparin, and tinzaparin. In some embodiments, the pharmaceutical composition contains heparin at the concentration of 0.00001 U to 20 U (e.g., 0.0001 to 10, 0.0001, 0.0005, 0.001, 0.005, 0.01, 0.05, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20 U) per 100 uL. One unit (U) of heparin (the "Howell unit") is an amount approximately equivalent to 0.002 mg of pure heparin, which is the quantity required to keep 1 ml of cat's blood fluid for 24 hours at 0° C.

The core component can further include a thrombolytic drug or angiogenic compound selected from the group consisting of VEGF, ticlopidine, warfarin, tissue plasminogen activator (t-PA), eminase (anistreplase), retavase (reteplase), streptase (streptokinase, kabikinase), activase, tenecteplase (TNKase), abbokinase, kinlytic (rokinase), urokinase, prourokinase, anisoylated plasminogen streptokinase activator complex (APSAC), fibrin, and plasmin. The pharmaceutical composition can include one or more thrombolytic drugs or angiogenic compounds. The pharmaceutical composition can contain the thrombolytic drugs and angiogenic compounds at dosages similar to or lower than recommended clinical dosages.

The term "hyaluronan" refers to a naturally-occurring anionic, non-sulfated glycosaminoglycan including repeated disaccharide units of N-acetylglucosamine and D-glucuronic acid, and its derivative. Naturally-occurring hyaluronan (also known as hyaluronic acid or hyaluronate) can be isolated from its natural sources, e.g., capsules of Streptococci, rooster comb, cartilage, synovial joints fluid, umbilical cord, skin tissue and vitreous of eyes, via conventional methods. See, e.g., Guillermo Lago et al. Carbohydrate Polymers 62(4): 321-326, 2005; and Ichika Amagai et al. Fisheries Science 75(3): 805-810, 2009. Alternatively, it can be purchased from a commercial vendor, e.g., Genzyme Corporation, Lifecore Biomedical, LLC and Hyaluron Contract Manufacturing. Derivatives of naturally-occurring hyaluronan include, but are not limited to, hyaluronan esters, adipic dihydrazide-modified hyaluronan, hyaluronan amide products, crosslinked hyaluronic acid, hemiesters of succinic acid or heavy metal salts thereof hyaluronic acid, partial or total esters of hyaluronic acid, sulphated hyaluronic acid, N-sulphated hyaluronic acid, and amines or diamines modified hyaluronic acid. They can be obtained by chemically modifying one or more of its functional groups (e.g., carboxylic acid group, hydroxyl group, reducing end group, N-acetyl group). A carboxyl group can be modified via esterification or reactions mediated by carbodiimide and bishydrazide. Modifications of hydroxyl groups include, but are not limited to, sulfation, esterification, isourea coupling, cyanogen bromide activation, and periodate oxidation. A reducing end group can be modified by reductive amination. It also can be linked to a phospholipid, a dye (e.g., a fluorophore or chromophore), or an agent suitable for preparation of affinity matrices. Derivatives of naturally-occurring hyaluronan can also be obtained by crosslinking, using a crosslinking agent (e.g., bisepoxide, divinylsulfone, biscarbodiimide, small homobifunctional linker, formaldehyde, cyclohexyl isocyanide, and lysine ethyl ester, metal cation, hydrazide, or a mixture thereof) or via internal esterification, photo-crosslinking, or surface plasma treatment. To make a hyaluronan solution, hyaluronan can be dissolved in a phosphate buffer solution (e.g., ≤0.05 M at pH 7±1) and/or NaCl (e.g., ≤0.9%).

The matrix component can contain one or more other matrix molecules, so long as the viscosity of the composition stays within the desired range. The matrix molecules can include gelatin, collagen, hyaluronan, fibronectin, elastin, tenacin, laminin, vitronectin, polypeptides, heparan sulfate, chondroitin, chondroitin sulfate, keratan, keratan sulfate, dermatan sulfate, carrageenan, heparin, chitin, chitosan, alginate, agarose, agar, cellulose, methyl cellulose, carboxyl methyl cellulose, glycogen and derivatives thereof. In addition, the matrix component can include fibrin, fibrinogen, thrombin, polyglutamic acid, a synthetic polymer (e.g., acrylate, polylactic acid, polyglycolic acid, or poly(lactic-co-glycolic acid), or a cross-linking agent (e.g., genipin, glutaraldehyde, formaldehyde, or epoxide).

Treatment Method

An effective amount of the pharmaceutical composition can be administered to a patient to treat an ischemic tissue. It can be administered (e.g., injected or applied) directly to or near the ischemic tissue (e.g., a muscle). The composition, which is gelatinous or viscous in consistency, is not administered intravenously.

The composition can be administered to a subject as needed, e.g., 1 to 5 times daily, 1 to 5 times per week, 1 to 5 times per month, for a suitable treatment period, e.g., 1 to 4 week, 1 to 12 months, or 1 to 3 years. It is preferable that it is administered as soon as possible after the ischemia or the ischemic damage has occurred (e.g., within 0 to 48 hours or 1-7 days).

The amount of the pharmaceutical composition administered should be sufficient to provide an effective dose of the therapeutic compound, e.g., a heparin, a thrombolytic drug, or an angiogenic compound. An effective dose for the heparin can be 0.00001 U to 20 U (e.g., 0.0001 to 10, 0.0001, 0.0005, 0.001, 0.005, 0.01, 0.05, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20 U) per 100 µl per gram body weight. An effective dose for the thrombolytic drug or angiogenic compound can be, for example 0.00001 to 10 µg (e.g., 0.00001 to 0.001, 0.001 to 0.005, 0.005 to 0.01, 0.05 to 0.1, 0.1 to 0.5, 0.5 to 1, 0.00001, 0.0001, 0.0005, 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10 µg) per gram of the body weight of the subject, depending on the efficacy of the thrombolytic drug.

"Treating" refers to administration of a pharmaceutical composition to a subject, who is suffering from or is at risk for developing a disorder, with the purpose to cure, alleviate, relieve, remedy, delay the onset of, prevent, or ameliorate the disorder, the symptom of the disorder, the disease state secondary to the disorder, or the predisposition toward the disorder. An "effective amount" refers to an amount of the composition that is capable of producing a medically desirable result in a treated subject. The treatment method can be performed alone or in conjunction with other drugs or therapies. The subject to be treated can be a human or a laboratory or domestic animal.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are herein incorporated by reference in their entirety.

Example 1: Diabetic Lower Limb Ischemia Mouse Model

All the following experiments performed were pre-approved by the Institutional Animal Care and Use Committees (IACUCs) at the National Cheng Kung University (NCKU). The C57BL/6 male mice were sourced from the NCKU Laboratory Animal Center or BioLASCO Taiwan Co., Ltd. They were housed in the animal facility of the NCKU Institute of Biotechnology for at least one week in order for them to adapt to the environment before experiments were performed.

This experimental animal model was established for studying therapeutics treatments for lower limb ischemia. Mice that were 6-8 months or older were treated with 50 mg/kg body weight of a streptozotocin (STZ) solution to induce type I diabetes in order to exhibit the characteristics of older age and slow-to-heal wounded diabetic tissues. Since low blood sugar levels in mice would interfere with the results, mice with blood sugar levels within the range of 400 mg/dl to 550 mg/dl were used for the experiments, and minute amount of insulin might be applied to mice to avoid life-threatening high blood sugar levels. In order to avoid possibility of self-regenerative neovascularization, the femoral artery and its peripheral blood vessels in the lower limbs of the mice were severed. The model removed the possibility of blood vessel regeneration without treatment, which allowed a more accurate assessment of the angiogenic ability of testing drugs.

To induce lower limb ischemia, a shaved diabetic mouse was placed in a gas anesthesia box with a ventilating gas that contained 1-3% isoflurane per liter of gas per minute. After the mouse was unconscious, it was moved to the surgical table and maintained under gas anesthesia. After fixing the limbs using breathable tapes, the mouse's body temperature was kept constant with a 37° C. heating pad. After the lower abdomen and limb of the mouse were disinfected, the skin of the limb was cut from a small opening at the left ankle to the thigh. Both ends of the two lateral vessels on the dorsal side of the mouse calf muscle were tied with surgical sutures, and the blood vessels were removed to block the blood flow of the dorsal vessels. The side branches and main vessels of the ventral femoral artery were then blocked. The end of the artery near the ankle and its surrounding vessels were tied by surgical suture to ensure that the femoral artery and peripheral blood flow were completely blocked.

After truncating the blood vessels, a pharmaceutical composition to be tested for its therapeutic effect on ischemia was applied on a tissue directly or injected into the gastrocnemius muscle at eight sites, and the surgical opening was sutured. The mouse was subcutaneously injected with 1 mg/kg body weight of ketorolac analgesic and lidocaine-HCl local anesthetic, and also administered with 1 ml of saline solution to relieve pain and provide hydration. Whenever necessary, a glucose solution was administered to maintain physical strength.

TABLE 1

Lower limb ischemia appearance score of a diabetic mouse.

| Score | Condition/Appearance |
|---|---|
| 0 | Thigh amputation |
| 1 | Thigh necrosis |
| 2 | Calf amputation |
| 3 | Calf necrosis |
| 4 | Ankle joint necrosis |
| 5 | Claw amputation |
| 6 | Claw necrosis |
| 7 | Multiple toes amputation |
| 8 | One toe amputation |
| 9 | Multiple toes necrosis |
| 10 | One toe necrosis |
| 11 | Multiple blackened toes |
| 12 | One blackened toe |
| 13 | Multiple blackened/broken nails |
| 14 | One blackened/broken nail |
| 15 | Normal |

At day 0, 1, 2, 3, 4, 5, 6, 7, 14, 21 and 28 post-surgery, the apparent appearance and blood flow of the lower limb in the mice were evaluated using the score system shown in Table 1 and laser Doppler flowmetry, respectively. Region of interest (ROI) was obtained from laser Doppler flowmetry with the area from thigh to the end nail. The ROI was then calculated as the ratio of the blood flow signal of the left lower limb to that of the untreated right lower limb post-surgery, and the ratio in percentage was normalized based on the blood flow signal taken before the operation.

Example 2: Regeneration Power of Non-Diabetic Tissues

Figure 1:
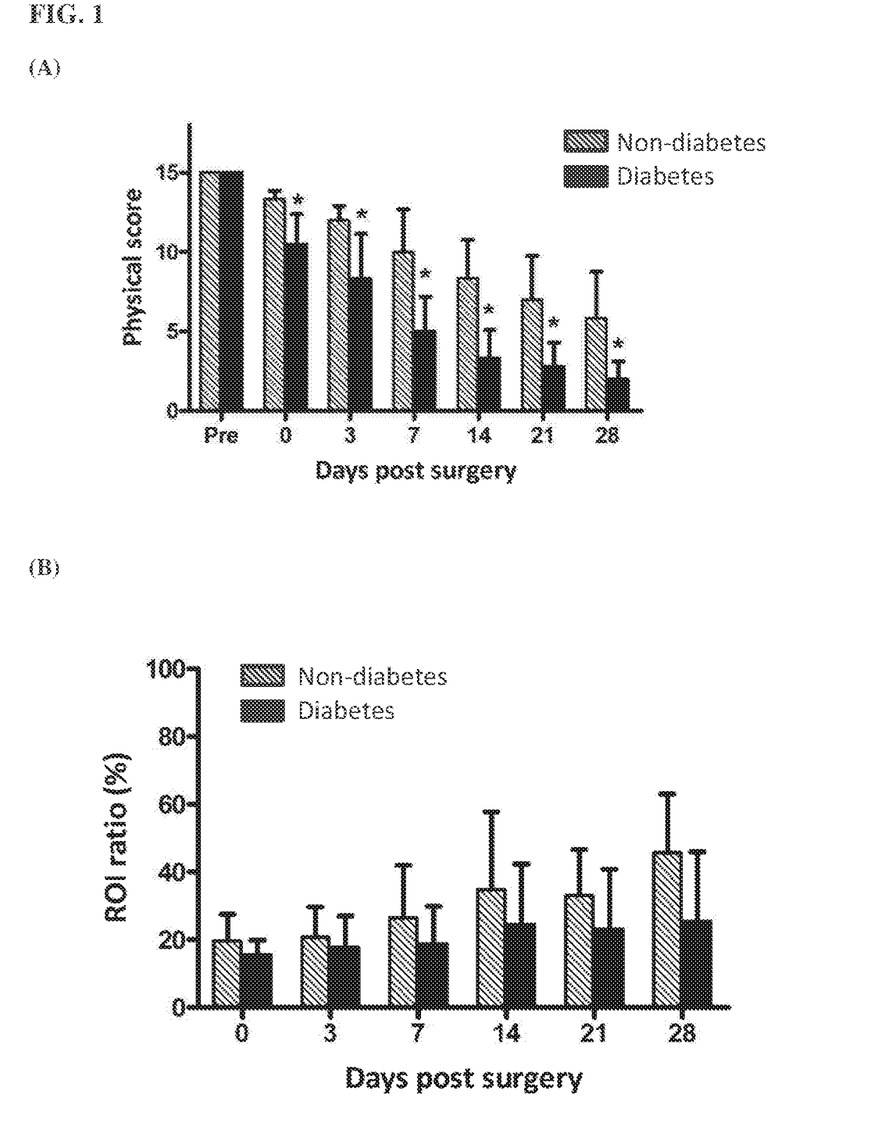
FIG. 1 is a set of bar graphs that compares the regenerative power of ischemic tissues in diabetic and non-diabetic mice. (A) lower limb physical scores; and (B) lower limb blood flow.

To compare the regeneration power of non-diabetic and diabetic mice, the surgery of lower limb ischemia described as above was performed on both groups of mice. The limb appearance scores and their blood flow information on both groups were recorded along with time. See FIGS. 1(A) and (B). Induction of diabetes in mice made the limb recovery worse than non-diabetic mice when both received severe ischemia surgery. The results also demonstrated that the blood flow in the lower limbs could be restored in the non-diabetic group better than the diabetic group. In order to screen and ensure that the efficacy of the pharmaceutical compositions, the diabetic mice were used in the following experiments but the results should not be used to restrict the application fields of the claims.

Example 3: Hyaluronan Viscosity Test

Compositions containing different concentrations of hyaluronan with various molecular weights were produced. The viscosity of the pharmaceutical compositions was tested using a DV2TRV Viscometer (Brookfield, USA) according to the manual. An appropriate spindle (CPE40 or CPE52) was selected according to the viscosity. Before testing, the machine was calibrated and set to run for 1 minute at 25° C. with 20 rpm. 500 μl of each sample was transferred with a viscosity pipette to the sample plate and the run button was pressed to start determining the viscosity of the sample.

The viscosities of the hyaluronan at 5 mg/ml with mean molecular wrights of 1,560 kDa, 700 kDa and 2,000 kDa were determined and the results are shown in Table 2. The viscosity of 5 mg/ml of hyaluronan with mean molecular wrights of 1,560 kDa was used as the reference, and the viscosities of various concentrations of hyaluronan with mean molecular wrights of 700 kDa and 2,000 kDa were measured as shown in Tables 3 and 4. The concentrations of hyaluronan with mean molecular wrights of 700 kDa and 2,000 kDa at a viscosity close to that of the reference viscosity were then calculated and adjusted to 6.5 and 4 mg/ml respectively.

As shown in Table 5 below, it was noticeable that the viscosity of hyaluronan with the same concentration and molecular weight range was changed when the measuring parameter changed.

TABLE 2

Viscosity of 5 mg/ml of hyaluronan with different molecular weights

| 5 mg/ml of hyaluronan | mean molecular wright of hyaluronan | | |
|---|---|---|---|
| (20 rpm) | 2000 kDa | 1560 kDa | 700 kDa |
| Viscosity (mPa · s) | 137.30 | 86.33 | 41.20 |
| Torque (%) | 84 | 52.8 | 25.2 |
| Shear stress (dyne/cm$^2$) | 206.0 | 129.5 | 61.8 |
| Shear rate (1/s) | | 150.0 | |

TABLE 3

Viscosity of hyaluronan at different concentrations with mean molecular weight of 700 kDa

| ~700 kDa of hyaluronan | Concentration of hyaluronan | | | |
|---|---|---|---|---|
| (20 rpm) | 5 mg/ml | 6 mg/ml | 7 mg/ml | 8 mg/ml |
| Viscosity (mPa · s) | 41.20 | 66.87 | 106.3 | 138.8 |
| Torque (%) | 25.2 | 40.9 | 65.0 | 84.9 |
| Sheer stress (dyne/cm$^2$) | 61.8 | 100.3 | 159.4 | 208.2 |
| Shear rate (1/s) | | 150.0 | | |

TABLE 4

Viscosity of hyaluronan at different concentrations with mean molecular weight of 2000 kDa

| ~2000 kDa of hyaluronan (20 rpm) | Concentration of hyaluronan | | | | |
|---|---|---|---|---|---|
| | 1 mg/ml | 2 mg/ml | 3 mg/ml | 4 mg/ml | 5 mg/ml |
| Viscosity (mPa · s) | 7.36 | 20.27 | 52.16 | 87.15 | 137.3 |
| Torque (%) | 4.5 | 12.4 | 31.9 | 53.3 | 84 |
| Sheer stress (dyne/cm$^2$) | 11.04 | 30.41 | 78.23 | 130.7 | 206.0 |
| Shear rate (1/s) | | | 150.0 | | |

TABLE 5

Viscosity of hyaluronan at different concentrations with a mean molecular weight of 1~1.8 MDa

| Viscosity of hyaluronan | Concentration of hyaluronan (mg/ml) | | | | | | |
|---|---|---|---|---|---|---|---|
| (mPa · s) | 1 | 2 | 3 | 4 | 5 | 6 | 7 |
| 50 rpm | 16.6 | 42.0 | 61.7 | 89.6 | 121.1 | — | — |
| | $Y = 25.66X - 10.77$, $R^2 = 0.9935$ | | | | | | |
| 10 rpm | 47.1 | 82.4 | 151.7 | 302.8 | 427.7 | 564.4 | — |
| | $Y = 130.8X - 222.37$, $R^2 = 0.9993$ | | | | | | |
| 2 rpm | 127.5 | 189.7 | 349.9 | 977.7 | 1436 | 1995 | 2596 |
| | $Y = 541.39X - 1226.5$, $R^2 = 0.9964$ | | | | | | |

Figure 2:
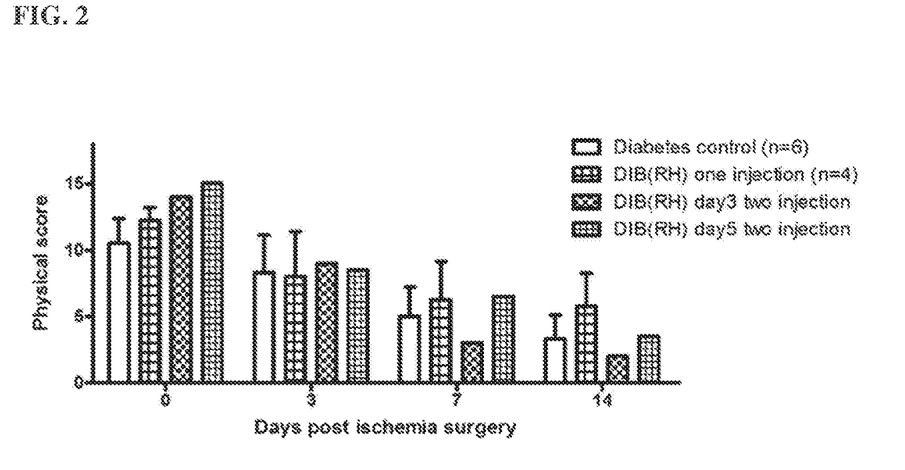
FIG. 2 is a bar graph that shows the appearance scores of diabetic mice with lower limb ischemia treated with a pharmaceutical composition containing hyaluronan.

Example 4: Efficacy of Hyaluronan or Heparin Alone on Treating Ischemic Tissues Hyaluronan was applied to the ischemic lower limb in diabetic mice through intramuscular injection. As shown in FIG. 2, hyaluronan alone had only a minor effect at 2 weeks but the effect was not significant when the diabetic mice had severe ischemia in the lower limbs. When a second injection was followed at day 3 or day 5, the multi-doses did not have any better therapeutic effect than the control group, which received phosphate buffer saline only to the ischemic sites. See FIG. 2.

Heparin is used for intravenous injection to prevent thrombosis. It was tested alone by injecting it into the ischemic sites of the lower limbs of the mice. Tissue bleeding was always seen surrounding the lower limbs of mice or no recovery effect was observed in the ischemic lower limbs of the mice (data not shown).

Example 5: Pharmaceutical Composition Containing Hyaluronan and Heparin

Pharmaceutical compositions each containing a core component of heparin and a hyaluronan matrix component were prepared and their therapeutic effects on ischemia were tested. The heparin component was one of the followings: unfractionated heparin (UFH), fractionated heparin (low molecular weight heparin), heparinoid, enoxaparin, dalteparin, and tinzaparin. The hyaluronan matrix component had a mean molecular weight of 4 to 5000 kDa. As described in Example 3, various molecular weights of hyaluronan at various concentrations gave different viscosities. Furthermore, heparin, especially UFH and heparinoid, are gelatinous materials and also provided certain viscosity.

The maximum and the minimum effective doses of the heparin drug that can be used in humans were converted to the dosages for mice according to their body weight. The pharmaceutical compositions were injected to multiple sites in diabetic mice after lower limb ischemic surgery as described in Example 1 above. Diabetic mice treated only with a buffer solution after surgery were used controls. The appearance scores were recorded at day 0, 1, 2, 3, 4, 5, 6, 7, 14, 21, and 28 post surgery and blood flow signals were determined at day 7, 14, 21, and 28 post surgery as described in Example 1 above.

In one instance, mean 2500 kDa of hyaluronan at 3.5 mg/ml and 0.1 U of low molecular weight heparin could prevent the ischemic limbs from severing. In another instance, mean 700 kDa of hyaluronan at 6.5 mg/ml and 0.05 U of heparinoid could prevent the ischemic limbs from severing.

Figure 3:
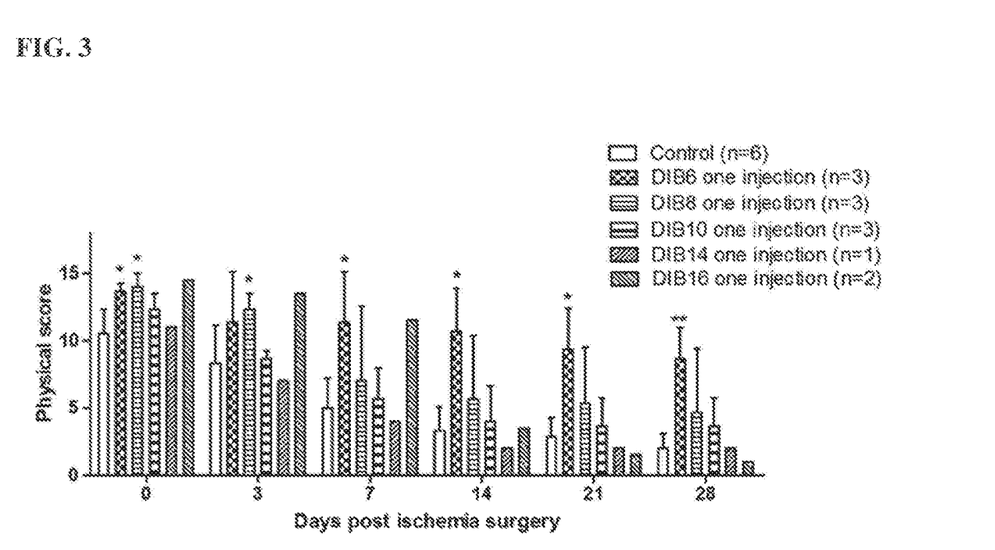
FIG. 3 is a bar graph that shows the appearance scores of diabetic mice with lower limb ischemia treated with pharmaceutical compositions containing hyaluronan and heparin.

Example 6: Efficacy of Pharmaceutical Compositions Containing Hyaluronan and Heparin Pharmaceutical compositions each containing a core component of low molecular weight heparin and 5 mg/ml of hyaluronan having a mean molecular weight of 1,560 kDa in a buffered phosphate saline solution were prepared and their therapeutic effects on lower limb ischemia were studied. The pharmaceutical compositions were administered to eight sites in the ischemic muscle of diabetic mice after lower limb ischemic surgery as described in Example 1. The diabetic mice treated only with phosphate buffer saline after the surgery were used as controls. The appearance scores were recorded at day 0, 1, 2, 3, 4, 5, 6, 7, 14, 21, and 28 post surgery and blood flow signals were determined at day 7, 14, 21, and 28 post surgery as described in Example 1 above. The appearances scores are shown in FIG. 3.

Treated mice were each injected with 100 μl of a pharmaceutical composition that contained 6 U, 8 U, 10 U, 14 U, or 16 U of low molecular weight heparin and 500 μg of hyaluronan having a mean molecular weight of 1,560 kDa (i.e., DIB6, DIB8, DIB10, DIB14, and DIB16, respectively). As shown in FIG. 3, the DIB6 group (6 U of low molecular weight heparin and hyaluronan) showed a significant therapeutic effect on the recovery or protection from gangrene of the ischemic lower limbs in diabetic mice. If converted to dosages used per body weight (BW), 0.20±0.01 U/g BW, 0.26±0.01 U/g BW, and 0.51±0.01 U/g BW of heparin were administered in the DIB6, DIB8, and DIB16 groups, respectively.

Example 7: Efficacy of Multiple Doses of Pharmaceutical Compositions Containing Hyaluronan and Heparin Diabetic mice were each injected post-surgery with 100 μl of a pharmaceutical composition that contained 2 U, 4 U, 6 U, 8 U, 10 U, 12 U, 14 U, or 16 U of low molecular weight heparin and 500 μg of hyaluronan having a mean molecular weight of 1,560 kDa (i.e., DIB2, DIB4, DIB6, DIB8, DIB10, DIB12, DIB14, and DIB16, respectively). In another word, 0.05-0.08 U/g BW, 0.12-0.15 U/g BW, 0.20±0.01 U/g BW, 0.26±0.01 U/g BW, and 0.51±0.01 U/g BW of heparin in the pharmaceutical compositions were administered in the DIB2, DIB4, DIB6, DIB8, and DIB16 groups, respectively.

Figure 4:
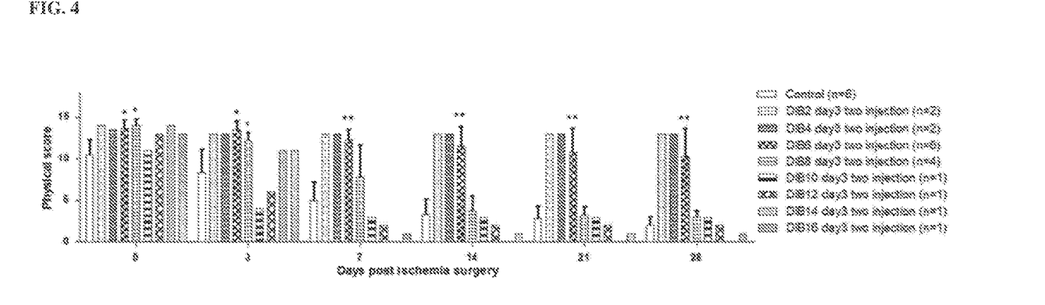
FIG. 4 is a bar graph that shows the appearance scores of diabetic mice with lower limb ischemia treated with multiple doses of pharmaceutical compositions containing hyaluronan and heparin.

The study was performed as described in Example 6 except that a second injection at multiple sites in the injured muscle was given at day 3 post surgery. The appearance scores of the lower limbs are shown in FIG. 4. The result demonstrated that 6 U or less of heparin in combination with hyaluronan provided therapeutic effects on ischemia and multiple doses could significantly increase the efficacy of the treatment.

Example 8: Optimal Doses of Heparin in the Pharmaceutical Compositions with Therapeutic Effects Various pharmaceutical compositions each containing low molecular weight heparin and hyaluronan were prepared as shown in Table 6, in which the heparin dosage is indicated as U/g body weight (BW). The compositions were administered to diabetic mice post ischemic surgery at multiple sites in ischemic muscle and observed as described in Example 6.

TABLE 6

Appearance scores of ischemic lower limbs in diabetic mice

| Mouse no. | Dosage (U/g BW) | \multicolumn{6}{c}{Day of post-surgery} | | | | | |
|---|---|---|---|---|---|---|---|
| | | 0 | 3 | 7 | 14 | 21 | 28 |
| 152804 | Control | 15 | 11 | 5 | 3 | 3 | 3 |
| 151303 | 8 U | 14 | 5 | 4 | 3 | 2 | 1 |
| 152705 | 8 U | 14 | 11 | 6 | 4 | 3 | 2 |
| 152801 | 6 U | 13 | 8 | 4 | 3 | 2 | — |
| 152001 | 6 U | 15 | 14 | 14 | 13 | 12 | 12 |
| 151801 | 3 U | 15 | 14 | 14 | 14 | 14 | 14 |
| 153304 | 0.12 U | 15 | 14 | 13 | 13 | 13 | — |
| 153202 | 0.5 U | 15 | 13 | 13 | 12 | 12 | 12 |
| 161403 | 0.05 U | 14 | 10 | 8 | 7 | 6 | 6 |
| 160402 | 0.01 U | 14 | 14 | 13 | 13 | 13 | 13 |
| 161207 | 0.005 U | 14 | 13 | 13 | 11 | 10 | 9 |
| 161205 | 0.001 U | 14 | 13 | 11 | — | — | — |
| 160102 | 0.0005 U | 15 | 13 | 12 | 11 | 10 | 10 |
| 161210 | 0.0001 U | 15 | 13 | 11 | 9 | 8 | 7 |

The appearance scores are shown in Table 6 above. The results demonstrated that 6 U/g BW or less of heparin with hyaluronan had therapeutic effects and effective dosages could range from 0.1 mU/g BW to 6 U/g BW, although some variations may be seen in different mice.

Example 9: Pharmaceutical Compositions Containing Different Types of Heparin, One or More Thrombolytic/Angiogenic Agents, and Hyaluronan Various pharmaceutical compositions containing combinations of different types of heparin, thrombolytic/angiogenic agents and hyaluronan were prepared as shown in Table 7. The compositions were administered to diabetic mice post ischemic surgery at multiple sites in ischemic muscle and observed as described in Example 6.

The appearance scores are shown in Table 7. The results demonstrated that the core component in the pharmaceutical composition could include various types of heparin and various thrombolytic/angiogenic agents, and effective doses of heparin could range from 0.00001 to 20 U/g BW. Yet, the pharmaceutical composition could include hyaluronan with a mean or average molecular weight ranging from 4 to 5000 kDa (e.g., 50 kDa to 2500 kDa).

TABLE 7

The appearance scores of lower limbs at day 28 post-surgery

| Core component | hyaluronan (avg. mw) | Score |
|---|---|---|
| Control | | 3~1 |
| heparin | 2500 kDa | 15~12 |
| | 1500 kDa | 15~13 |
| | 700 kDa | 15~13 |
| | 50 kDa | 14~10 |
| LMW heparin | 50 kDa~2500 kDa | 15~12 |
| Heparinoid | 50 kDa~2500 kDa | 15~10 |
| Heparin + ticlopidine | 50 kDa~2500 kDa | 15~13 |
| Heparin + warfarin | 50 kDa~2500 kDa | 15~13 |
| LMW heparin + ticlopidine | 50 kDa~2500 kDa | 15~13 |
| LMW heparin + warfarin | 50 kDa~2500 kDa | 15~13 |
| LMW heparin + VEGF | 50 kDa~2500 kDa | 15~13 |
| Heparinoid + ticlopidine | 50 kDa~2500 kDa | 15~13 |
| Heparinoid + warfarin | 50 kDa~2500 kDa | 15~13 |
| Heparin + ticlopidine + warfarin | 50 kDa~2500 kDa | 15~13 |
| Heparin + LMW heparin + warfarin | 50 kDa~2500 kDa | 15~13 |

The amount of heparin core component is 0.00001 to 20 U/g BW of heparin, LMW heparin, or heparinoid.

Although some variations may arise from individual to individual, the combination effects of hyaluronan and core component are partly through the interaction of viscous hyaluronan and core component to control the release of the effective ingredients in order to sustaining therapeutic effects without causing tissue bleeding.

Example 10: Functional Evaluation of Mice Treated with a Pharmaceutical Composition Since positive results were observed in the experiments described in Examples 6 to 9, physiological functions of the lower limbs at day 28 after ischemic surgery were investigated in order to understand the therapeutic effects of the pharmaceutical compositions. Imaging analysis showed that neovascularization obviously occurred in the DIB treatment groups (data not shown). It was observed from different staining of histology that local application of the pharmaceutical composition not only increased the efficacy of neovascularization, but the damage tissues were protected from gangrene.

Figure 5:
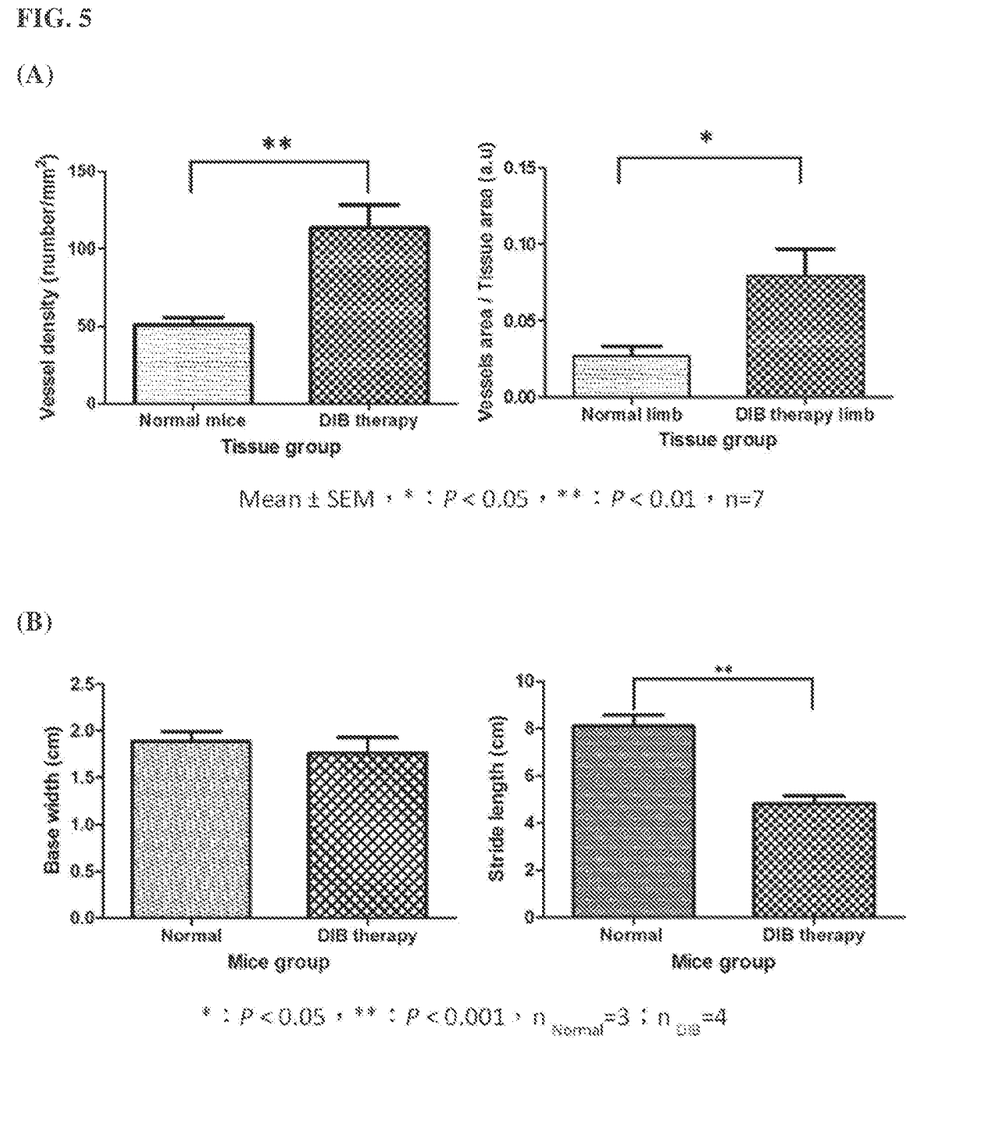
FIG. 5 is a set of bar graphs that shows (A) neovascularization and (B) walking function in diabetic mice with lower limb ischemia treated with a pharmaceutical composition containing hyaluronan and heparin.

A quantitative comparison between the neovascularization in the DIB treatment group at day 35 post surgery and that in normal mice is shown in FIG. 5(A). The results demonstrated that it took time to regenerate ischemic tissues, and proliferated vessels in terms of density and vessel diameter were observed at the same time the tissue regenerated. It was quite possible that the density and dimension of neo-vessels may approach normal given more time.

To further understand the regeneration of nerve functions, each mouse was placed on a platform and gait walking analysis was performed at day 35 post surgery. The results are shown in FIG. 5(B). It was observed that the base width between two limbs in the DIB treatment groups were no difference from that of the normal control group. Although the stride length of the DIB group significantly increased as compared with that of the control group, it was still from that of the normal mice. See FIG. 5(B). Since it took time for the walking function of damage limbs to recover, the results showed that, as the lower limbs of the mice in the DIB group started to atrophy after the surgery, their steps have not completely returned to normal, but they were still significantly better than the control group.

Example 11: Therapeutic Effects of a Pharmaceutical Composition on the Regeneration of Ischemic Heart Tissue after Infraction From the above experimental experiences, a pharmaceutical composition comprising 10 U/ml of heparin and 5 mg/ml of hyaluronan with a mean molecular weight of 1500 kDa was prepared for the heart infraction experiment. Diabetic symptom in Lanyu pigs at 12- to 18-month old was induced by alloxan injection. The regenerative ability of diabetic pigs was significantly lower than that of the normal control. Myocardial surgery was performed on the coronary artery of a pig heart, and the vessel in the upper diagonal branch D2 of left anterior descending (LAD) was ligated. After the ischemia surgery, 30 to 40 sites at the ischemic myocardium were administered with the gelatinous pharmaceutical composition as prepared above by intramuscular injection. Echocardiography and angiography were used to observe heart function and vascular response, respectively. Sonography was performed every week.

Figure 6:
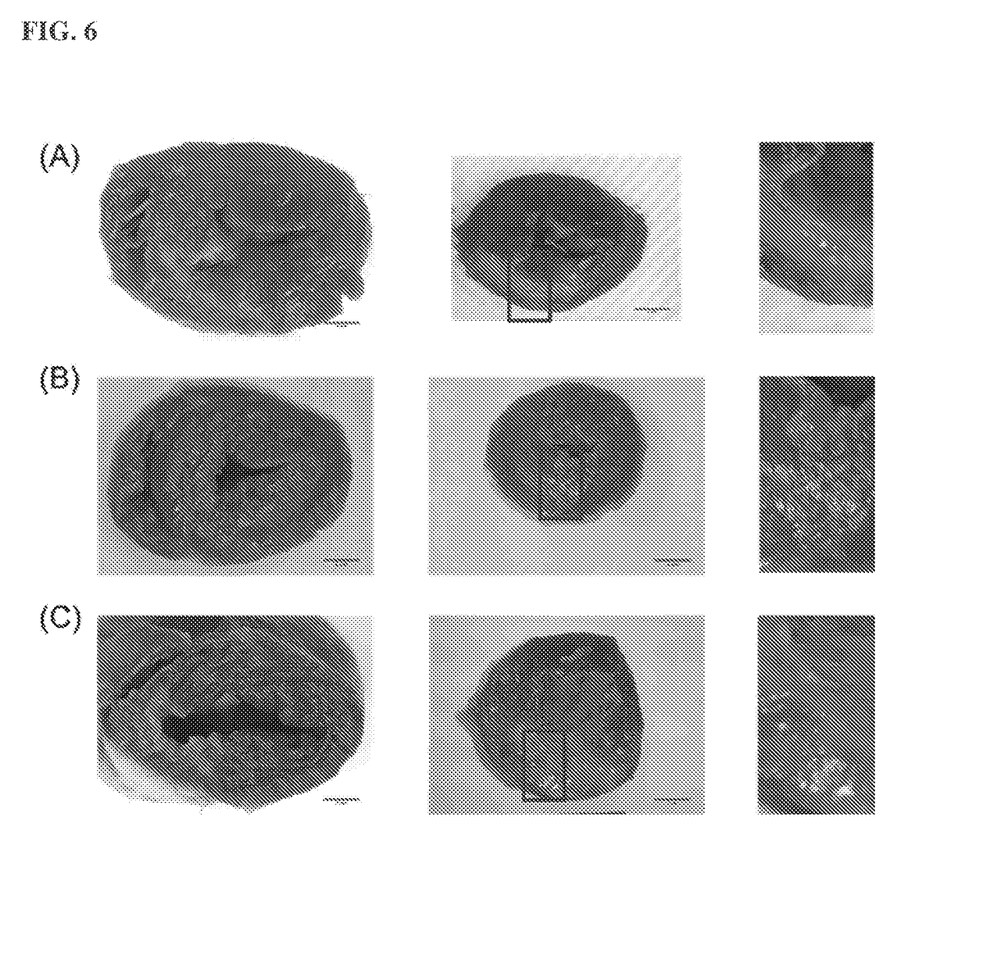
FIG. 6 is a set of images showing cross sections of ischemic pig hearts treated with (A) a buffer solution, (B) a pharmaceutical composition containing heparin and hyaluronan, and (C) a pharmaceutical composition containing heparin and hyaluronan having the one-third of the viscosity of the composition of (B).

FIG. 6 shows cross sections of the apical sides at the lower edge of ligation. The myocardium next to the coronary artery of ligation was amplified for comparison of the fibrosis area. (scale bar=1 cm). It was observed that, at day 28 post surgery, treatment with the pharmaceutical composition gave a remarkable result that no fibrosis tissue was observed in the myocardium, although the ligation knots were still present in the heart. On the other hand, fibrosis tissues were obvious in both the sham control group and the other experimental group in which the viscosity of the pharmaceutical composition was reduced purposely to one third of the preferred pharmaceutical composition by dilution with phosphate buffered saline solution. Furthermore, the heart was collected after being sacrificed for subsequent histology staining. These results also suggest that a certain range of viscosity is optimal.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

What is claimed is:

1. A pharmaceutical composition for treating an ischemic tissue, comprising:
   a heparin or derivative thereof and a hyaluronan or derivative thereof, and optionally, one or more optional molecules selected from the group consisting of ticlopidine, warfarin, tissue plasminogen activator, anistreplase, reteplase, streptokinase, teneteplase, urokinase, prourokinase, fibrin, plasmin, a collagen, and a gelatin, the pharmaceutical composition having a viscosity greater than 10 mPa·s as measured at 20 rpm and 25° C.,
   wherein the heparin or derivative thereof, the hyaluronan or derivative thereof, and the one or more optional molecules are the sole active ingredients,
   wherein the hyaluronan has a mean molecular weight of 100 kDa to 5000 kDa; and
   wherein the pharmaceutical composition contains the heparin or derivative thereof at 0.0001 U to 3 U per 100 µl.

2. The pharmaceutical composition of claim 1, wherein the viscosity is 10 to 10000 mPa·s.

3. The pharmaceutical composition of claim 1, wherein the hyaluronan has a mean molecular weight of 700 kDa to 2000 kDa.

4. The pharmaceutical composition of claim 1, wherein the pharmaceutical composition contains 1 mg/ml to 100 mg/ml of the hyaluronan.

5. The pharmaceutical composition of claim 1, wherein the viscosity is within the range of viscosities of 3 to 10 mg/ml of hyaluronan having a mean molecular weight of 700 to 2000 kDa as measured at 20 rpm and 25° C.

6. The pharmaceutical composition of claim 1, wherein the viscosity is the same as the viscosity of 5 mg/ml of hyaluronan having a mean molecular weight of 1560 kDa as measured at 20 rpm and 25° C.

7. The pharmaceutical composition of claim 5, wherein the mean molecular weight of the hyaluronan is 700 to 2000 kDa and the concentration of the hyaluronan is 3 to 10 mg/ml.

8. The pharmaceutical composition of claim 6, wherein the mean molecular weight of the hyaluronan is 1560 kDa and the concentration of the hyaluronan is 5 mg/ml.

9. The pharmaceutical composition of claim 1, wherein the pharmaceutical composition includes a collagen, or a gelatin.

10. The pharmaceutical composition of claim 1, wherein the heparin or derivative thereof is selected from the group consisting of unfractionated heparin (UFH), fractionated heparin (low molecular weight heparin), heparinoid, enoxaparin, dalteparin, or tinzaparin.

11. The pharmaceutical composition of claim 1, wherein the pharmaceutical composition contains the heparin or derivative thereof at 0.0001 U to 2 U per 100 µl.

12. A pharmaceutical composition of claim 1, wherein the pharmaceutical composition includes one or more compounds selected from the group consisting of ticlopidine, warfarin, tissue plasminogen activator, anistreplase, reteplase, streptokinase, teneteplase, urokinase, prourokinase, fibrin, and plasmin.

13. The pharmaceutical composition of claim 1, wherein the pharmaceutical composition is directly administered to the ischemic tissue but is not administered intravenously.

14. The pharmaceutical composition of claim 13, wherein the ischemic tissue is an ulcer, or in a heart or limb in a subject.

15. A method of treating an ischemic tissue in a subject, comprising:
   administering a pharmaceutical composition of claim 1 directly to the ischemic tissue, provided that the pharmaceutical composition is not administered intravenously.

16. The method of claim 15, wherein the ischemic tissue is an ulcer or in a heart or limb.

17. The method of claim 15, wherein the ischemic tissue is a muscle.

18. The method of claim 15, wherein the subject has diabetes.

19. The method of claim 15, wherein the matrix component has a viscosity no greater than 10000 mPa·s.

* * * * *